United States Patent
Tsai et al.

(10) Patent No.: US 7,400,401 B2
(45) Date of Patent: Jul. 15, 2008

(54) MEASURING LOW DIELECTRIC CONSTANT FILM PROPERTIES DURING PROCESSING

(75) Inventors: Jang-Shiang Tsai, Shindian (TW); Peng-Fu Hsu, Hsinchu (TW); Baw-Ching Perng, Hsin-Chu (TW); Ju-Wang Hsu, Taipei (TW); Jyu-Horng Shieh, Hsin-Chu (TW); Yi-Nien Su, Kaohsiung (TW); Hun-Jan Tao, HsinChu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 92 days.

(21) Appl. No.: 11/096,049

(22) Filed: Mar. 31, 2005

(65) Prior Publication Data

US 2006/0220653 A1   Oct. 5, 2006

(51) Int. Cl.
*G01J 4/00* (2006.01)
(52) U.S. Cl. .................. 356/369; 356/445; 356/326
(58) Field of Classification Search ................ 356/326, 356/328, 357, 359, 360, 371, 381, 517, 491, 356/450, 484, 487, 485, 128, 369, 631, 630, 356/600, 601, 445; 250/339.07, 339.08, 250/374; 436/518
See application file for complete search history.

(56) References Cited

U.S. PATENT DOCUMENTS

| | | | | |
|---|---|---|---|---|
| 4,905,170 A | * | 2/1990 | Forouhi et al. ............... | 356/631 |
| 5,463,226 A | * | 10/1995 | Matsuzaki et al. .......... | 250/374 |
| 5,631,171 A | * | 5/1997 | Sandstrom et al. ........... | 436/518 |
| 6,052,191 A | * | 4/2000 | Brayden et al. .............. | 356/630 |
| 6,511,922 B2 | * | 1/2003 | Krishnaraj et al. ........... | 438/778 |
| 6,829,054 B2 | * | 12/2004 | Stanke et al. ................. | 356/601 |
| 6,862,095 B2 | * | 3/2005 | Horie .......................... | 356/445 |
| 2002/0180986 A1 | * | 12/2002 | Nikoonahad et al. ........ | 356/600 |
| 2004/0004484 A1 | | 1/2004 | Talanov et al. | |

OTHER PUBLICATIONS

Kinder et al., "The influence of the electrolyte-semiconductor interface on the doping profile measurement of a GaAs structure", ASDAM 2000, pp. 336-337, Published in 2000.*

Han, Sang M., "Reasons for lower dielectric constant of fluorinated SiO2 films", Journal of Applied Physics, vol. 83, No. 4, Feb. 15, 1998, pp. 2172-2178.*

Narasimhan, Murali, "Taking Control of the Copper Process at 65 nm", http://www.future-fab.com/documents.asp?d_ID=2365 , Feb. 3, 2004, pp. 1-11.*

(Continued)

*Primary Examiner*—Tarifur R Chowdhury
*Assistant Examiner*—Jonathan M Hansen
(74) *Attorney, Agent, or Firm*—Duane Morris LLP

(57) ABSTRACT

A method and system for determining the dielectric constant of a low-k dielectric film on a production substrate include measuring the electronic component of the dielectric constant using an ellipsometer, measuring the ionic component of the dielectric constant using an IR spectrometer, measuring the overall dielectric constant using a microwave spectrometer and deriving the dipolar component of the dielectric constant. The measurements and determination are non-contact and may be carried out on a production device that is further processed following the measurements.

17 Claims, 1 Drawing Sheet

OTHER PUBLICATIONS

Yee Wee Koh et al., "Low Dielectric Constant a-SiOC:H Films As Copper Diffusion Barrier", Journal Of Applied Physics, vol. 93, No. 2, Jan. 15, 2003, pp. 1241-1245.

Scott Baumann, "Outsourcing Of Analysis: Choosing The Right Technique", Evans Analytical Group/Evans Texas at http://www.eaglabs.com/Choosing%20Right%20Technique.pdf, 12 pages.

Vladimir V. Talanov et al., "Scanning Near-Field Microwave Probe For In-Line Metrology Of Low-K Dielectrics", Mat. Res. Soc. Symp. Proc. vol. 812, 2004 Materials Research Society, pp. F5.11.1-F5.11.6.

Koya Ohara et al., "Quantitative Measurement Of Linear Dielectric Constant Using Scanning Nonlinear Dielectric Microscopy With Electro-Conductive Cantilever", Jpn. J. Appl. Phys. vol. 41 (2002) pp. 4961-1964, Part 1, No. 7B, Jul. 2002, 2002 The Japan Society Of Applied Physics.

C. Gao et al., "Quantitative Microwave Near-Field Microscopy Of Dielectric Properties", Review Of Scientific Instruments, vol. 69, No. 11, Nov. 1998, 1998 American Institute Of Physics, pp. 3846-3851.

A. F. Lann et al., Microwave Near-Field Polarimetry, Applied Physics Letters, vol. 75, No. 5, Aug. 2, 1999, 1999 American Institute of Physics, pp. 603-605.

C. P. Vlahacos et al., Near-Field Scanning Microwave Microscope With 100 um Resolution, Appl. Phys. Lett. 69 (21), Nov. 18, 1996, 1996 American Institute Of Physics, pp. 3272-3274.

* cited by examiner

MEASURING LOW DIELECTRIC CONSTANT FILM PROPERTIES DURING PROCESSING

FIELD OF THE INVENTION

The present invention is related to measuring the dielectric constant of a low-k dielectric film, and in particular measuring to determine the various component of the dielectric constant.

BACKGROUND

In the semiconductor device manufacturing industry, advanced semiconductor high performance integrated circuits require that the materials used as interlayer and intermetal dielectrics decrease the RC delay of the interconnects and also reduce the crosstalk between metal lines. Low dielectric constant (low-k) materials have been developed and continue to be developed for this purpose. The particular dielectric constant of the materials used for interlayer or intermetal dielectrics is critical for device performance. It is therefore imperative to accurately measure the dielectric constant of a formed low-k dielectric film. It would be advantageous to measure the dielectric constant on a product substrate during processing, i.e., a substrate that continues to be processed and to have integrated circuits or other semiconductor devices formed thereon. It would also be advantageous to be able to measure the dielectric constant without having to form a particular structure dedicated to such measurement. Finally, it would be advantageous to measure the dielectric constant in a manner that does not damage or alter the film.

Present methods for measuring dielectric constant include use of a mercury (Hg) probe. This technique requires a specific MOS structure to be created for such measurement. Furthermore, a mercury dot contacts a surface of a low-k film producing contamination concerns for further processing. The surface contact may furthermore bring about other film quality maintenance concerns. Another method for measuring dielectric constant is the MIS (metal-insulator-semiconductor) (CAT) but this also requires a specific MOS structure for measurement and requires a formation of a metal electrode on the substrate. Yet another technique is the interdigitated comb which requires the formation of an interdigitated comb structure on the substrate. While the interdigitated comb technique produces accurate data, data collection is not real-time as the substrate being measured must be removed from production because the dielectric constant extraction requires extensive cross-sectioning and Raphael modeling. In sum, the shortcomings of conventional techniques for measuring the dielectric constant of a low-k dielectric film include surface contact, the requirement to produce a particular dedicated measurement structure, the lack of real-time data and the requirement to permanently remove the tested substrate from the production environment.

The dielectric constant is a frequency dependent, intrinsic material property. It consists of three components that result from electronic, ionic and dipolar polarization. The individual components of the overall dielectric constant are impacted by different phenomena and processees associated with semiconductor device manufacturing. It would therefore be desirable to measure or derive each of the three components as well as the overall dielectric constant.

It would therefore be ultimately desirable to provide a non-contact measurement technique that yields each of the components of the dielectric constant and the overall dielectric constant of a low-k dielectric film for a substrate that continues to be processed and which does not require formation of a particular test structure.

SUMMARY OF THE INVENTION

To address these and other needs and in view of its purposes, the invention provides a method for determining dielectric constant of a film. The method includes providing a low-k dielectric film over a reflective layer formed over a substrate, determining dielectric constant of the low-k dielectric film by measuring the dielectric constant without contacting the low-k dielectric film. The measuring includes separately measuring an electronic component of the dielectric constant, an ionic component of the dielectric constant and an overall dielectric constant, and deriving a dipolar component of the dielectric constant from the electronic component, the ionic component, and the overall dielectric constant.

Another aspect of the invention provides a method for determining dielectric constant of a low-k dielectric film. The method includes providing a low-k dielectric film over a reflective layer formed over a substrate, determining an overall dielectric constant, an electronic component of the dielectric constant, an ionic component of the dielectric constant and a dipolar component of said of the dielectric constant by first measuring using an ellipsometer, secondly measuring using an infrared spectrometer and thirdly measuring using a microwave spectrometer and mathematically manipulating results of the first, second and third measurements.

Another aspect of the invention provides a system for measuring dielectric constant of a low-k dielectric film formed over a reflective layer. The system includes an ellipsometer that measures an electronic component of the dielectric constant of the low-k dielectric film and produces a measured electronic component, an infrared spectrometer that measures an ionic component of the dielectric constant of the low-k dielectric film and produces a measured ionic component and a microwave spectrometer that measures an overall dielectric constant of the low-k dielectric film and produces a measured overall dielectric constant. The system further includes means for deriving a dipole component of the dielectric constant using the measured electronic component, the measured ionic component and the measured overall dielectric constant.

BRIEF DESCRIPTION OF THE DRAWING

The present invention is best understood from the following detailed description when read in conjunction of the accompanying drawing. It is emphasized that, according to common practice, the various features of the drawing are not necessarily to scale. On the contrary, the dimensions of the various features are arbitrarily expanded or reduced for clarity.

DETAILED DESCRIPTION

Figure 1:
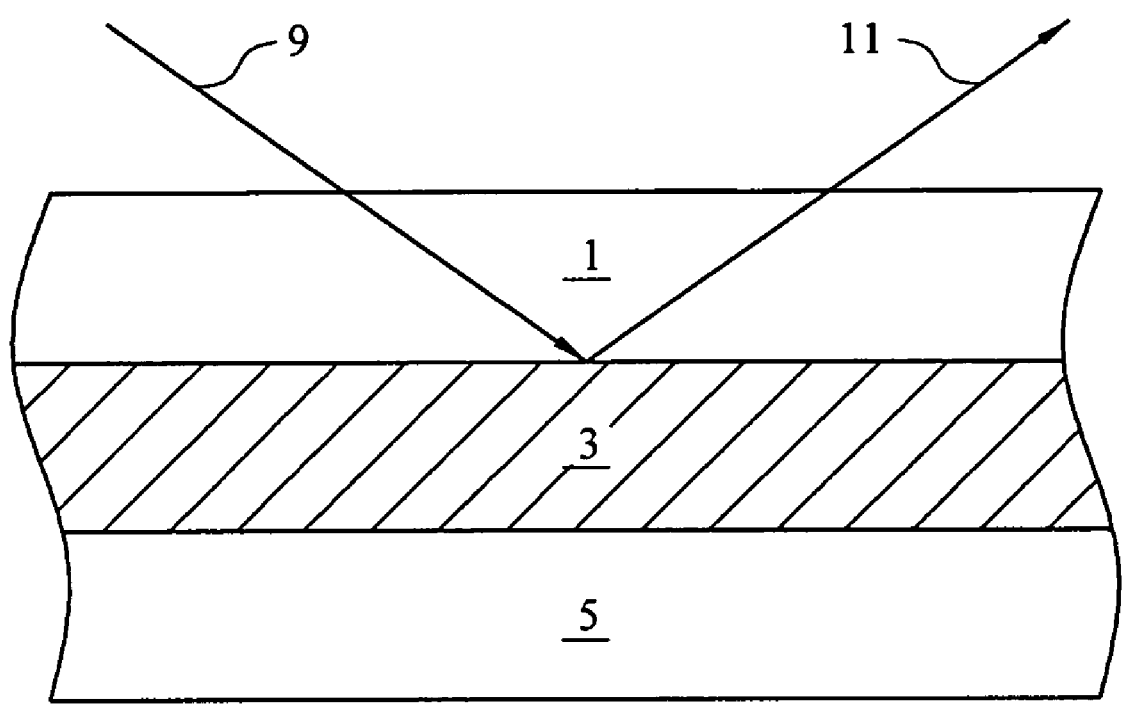
FIG. 1 is a cross sectional view of a low-k dielectric film being measured.

The present invention provides for determining the overall dielectric constant and the various components of the dielectric constant of a low-k film formed on a semiconductor substrate. Various semiconductor substrates, such as a silicon wafer, may be used and various films, devices, structures and impurity regions may be formed over the substrate and patterned using the sequence of processing operations that forms a semiconductor integrated circuit or other semiconductor device. At various stages of the processing sequence, a low-k dielectric film may be used as an interlevel or intermetal dielectric. SiOC and SiOC:H are examples of low-k dielectric films but various low-k dielectric films may be used and measured according to the present invention. The present invention provides for making non-contact measurements of a dielectric film of a production device to yield the overall dielectric constant, the electronic component, the ionic component and the dipolar component of the dielectric constant. The non-contact measurements do not damage or alter the measured films. The dielectric constant of the low-k dielectric film may be evaluated at any place on the substrate where the low-k dielectric film is disposed over a reflective layer. A particular test structure for dielectric constant measurement is not required. The measurements may be done during processing, the substrate need not be removed from the processing environment and after the measurements are carried out, further processing operations may be performed on the substrate to complete the integrated circuit or other semiconductor devices.

Dielectric constant is a frequency dependent, intrinsic material property. It consists of three components that result from electronic, ionic, and dipolar polarization. The electronic contribution arises from the polarization created by the distortion of the electron clouds surrounding the nuclei that make up the solid. The ionic contribution results from the polarization caused by the motions of the nuclei with respect to each other, and the dipolar contribution arise when the moieties with dipole moments orient themselves with the applied field. The individual contributions are measured at various wavelengths using various techniques. The dielectric constant may be measured in the visible-to-UV range at wavelengths 300-750 nm; in the infrared region at wavelengths of 2-15 um; and in the microwave regime at frequencies of 1-15 GHz. Spectroscopic ellipsometry may be used to measure electronic polarization in the visible-to-UV region. The dielectric constant in the infrared region may advantageously be calculated from the infrared absorption spectra using the Kramer-Kronig dispersion relations and the results were used to determine the ionic contribution. In microwave region, the three polarization phenomena contribute to the total dielectric constant which may be measured by the difference between incident and reflective microwave signal. The dielectric constant measured in the microwave region is expressed in Eq. (1):

$\epsilon_r(\text{at 1-15 GHz}) = 1 + \Delta\epsilon_e + \Delta\epsilon_i + \Delta\epsilon_d$.

where the ionic contribution to the dielectric constant is $\Delta\epsilon_i$, the electronic contribution to the dielectric constant is $\Delta\epsilon_e$ and the dipolar contribution to the dielectric constant is $\Delta\epsilon_d$. The dielectric constant of a material can also be calculated from the refractive index, as expressed in Eq. (2):

$\epsilon_r(\lambda) = n^2(\lambda) - k^2(\lambda)$, where $\epsilon_r$ is a relative dielectric constant, n is a real part of a refractive index, k is an imaginary part of a refractive index, and $\lambda$ is the wavelength of a light source.

If the wavelength of the light source is in the visible to ultraviolet (UV) range, only electrons can respond to the time varying fields, and the dielectric constant in this range is solely due to the electronic polarization. The pure electronic contribution can be calculated from the refractive index obtained in the visible-ultraviolet (vis-UV) region, in which the pure electronic contribution of the dielectric constant is equal to the square of the refractive index.

The ionic contribution to the dielectric constant ($\Delta\epsilon_i$) may be calculated by subtracting the dielectric constant in the visible-uv range (<700 nm) for example at 633 nm, $1+\Delta\epsilon_e$, from the dielectric constant in the IR region (>1300 nm), $1+\Delta\epsilon_e+\Delta\epsilon_i$. The Kramers-Kronig dispersion relation may be used to calculate the refractive index in the IR region.

The original Kramers-Kronig relation is expressed in Eq. (3):

$$n_i = 1 + \frac{\pi}{2} p \int_0^\infty \frac{v k(v)}{v^2 - v_i^2} dv,$$

where $n_i$ is the real part of the refractive index at $v_i$. P indicates the principle value of ensuring integral from zero to infinity. The integration above cannot be performed from zero to infinity because the absorbance spectra can be taken only in a finite region of the IR spectrum.

The effect of various processing operations upon the various components of the dielectric constant can be evaluated by measuring or otherwise determining all of the components and the overall dielectric both before and after a processing operation. The difference in the overall dielectric constant, the electronic component, the ionic component, and the dipolar component of the dielectric constant can be evaluated by comparing values before and after the operation and it can then be understood that the particular processing operation affects a particular aspect, i.e., component, of the dielectric constant. Since the various components of the dielectric constant are known to be caused by different phenomena, as above, the particularized impact of a processing operation can be better understood.

FIG. 1 is a cross sectional view showing low-k dielectric film 1 formed over substrate 5. In particular, low-k dielectric film 5 is formed on reflective layer 3 which, in turn is formed on substrate 5. This is intended to be exemplary only and various other films may be interposed between reflective layer 3 and substrate 5. Reflective layer 3 may be copper, aluminum or other suitable metal materials that may serve as interconnect features in the semiconductor device. The dielectric constant measurement and the illustrated location may be any place on the substrate, such as an isolated portion of an otherwise congested integrated circuit. Substrate 5 may be a production wafer that continues to be processed after the dielectric constant measurement and the illustrated location may be any place on the substrate. Incident radiation 9 and reflected radiation 11 may represent radiation of various wavelengths used in the present invention with a suitable radiation generator and detector. The present invention provides for separately measuring the electronic component of the dielectric constant using an ellipsometer, measuring the ionic component of the dielectric constant using an IR (infrared) spectrometer and for measuring the overall dielectric constant using a microwave spectrometer. The dipolar component of the dielectric constant is then calculated according to the relationship discussed above.

A conventional ellipsometer may be used to measure the electronic component of the dielectric constant. Light in the visual-ultraviolet range is used. Measurements are made using conventional techniques and over a wide range of frequencies, or wavenumbers, in the visible-UV range. The ellipsometer measures the electronic component of the dielectric constant by measuring refractive index of the low-k dielectric material and calculating the dielectric constant according to equation (2) above.

The ionic component of the dielectric constant is obtained using an infrared spectrometer that utilizes radiation over a range of wavenumbers in the infrared spectrum. The Kramers-Kronig dispersion relation is used to calculate the refractive index in the IR region as above. The dielectric constant is obtained from the refractive index and the extinction coefficient, as above, and the ionic contribution to the dielectric constant is calculated as above.

The overall dielectric constant may be obtained using a microwave spectrometer that utilizes microwaves and makes a plurality of measurements across a wide range of wavenumbers. A non-contact microwave signal source is used along with a suitable detector. The measurement is made in the microwave range of frequencies such as 4 GHz, but other frequencies may be used alternatively. In one embodiment, the microwave and IR measurements may be made by the same spectrometer tool. A technique for measuring the dielectric constant of low-k dielectric films using microwave spectroscopy and non-contact measurements is available in Talanov, *Scanning Near-Field Microwave Probe For In-Line Metrology of Low-k Dielectrics*, Mat. Res. Soc. Symp. Proc. Dol. 812, 2004 Materials Research Society page F5.11.1-F5.11.6. which describes a non-contact measurement technique with high resolution (a few microns spot size) that can be made on a patterned production wafer. One exemplary advantageous technique involves a near-field non-contact probe measuring dielectric constant according to the following.

According to the microwave technique, when the probe tip is placed in close proximity to the sample under test, its fringe capacitance $C_1$ is governed by the tip geometry, the same permittivity, and the tip-sample distance. The complex reflection coefficient from the tip can be found as follows (Eq. 4):

$$\Gamma \cong exp(-i\omega Z_0 C_1)$$

where $\omega$ is the operating frequency, $Z_0$ is the line characteristic impedance, and $\omega Z_0 C \ll 1$. In order to increase the measurement sensitivity, the transmission line may be formed into a half-lambda resonator by etching the back end of the aluminum strips to the appropriate length. The resonator has a resonant frequency F~4 GHz and an unloaded quality factor Q~100. A conventional magnetic loop is used to couple the microwave signal into it. The resonator is packaged inside a metallic enclosure with the tapered portion protruding out through a clear hole in the enclosure wall. The probe resonant frequency F is experimentally determined from the minimum in the probe reflection coefficient $S_{11}$ using a microwave reflectometer with resolution down to 100 Hz.

From Eq. (5) we find the relative shift in the probe resonant frequency F versus change in the tip capacitance $C_t$:

$$\frac{\Delta F}{F} = -\frac{Z_0}{L\sqrt{\varepsilon_0 \mu \varepsilon_{\mathit{eff}}}} \Delta C_t$$

where L is the resonator length, $\varepsilon_0$ is vacuum permittivity, $\mu_0$ is vacuum permeability, $\varepsilon_{\mathit{eff}}$ is the transmission line effective dielectric constant, and $Z_0$ is the line characteristic impedance in Equation 5. An estimate for the tip capacitance in air is $C_{t0} \sim \varepsilon_0 \alpha_t$, where $\alpha_t$ is the tip size; for $\alpha_t \sim 1$ µm $C_{t0} \sim 10$ aF. For typical probe parameter (L~25 mm, $Z_0$~100 Ω, $\varepsilon_{\mathit{eff}}$~2.5) and a 100 Hz precision in $\Delta F$, Eq. (5) yields sensitivity to changes in the tip capacitance on the order of $3 \times 10^{-20}$F=30 zF.

With the overall dielectric constant obtained using microwave spectroscopy, the electronic component of the dielectric constant obtained using an ellipsometer and the ionic component of the dielectric constant obtained using an IR spectrometer, the dipolar component of the dielectric constant may be derived according to Eq. (1), above. A computer may be used to perform the calculation or the values may be mathematically manipulated using other means.

After the measurements are carried out, processing may continue on the substrate and the integrated circuits devices may be completed. The method may advantageously be carried out on the same film before and following a processing operation to yield overall dielectric constant and component values before and after the processing operation. The before and after results may be compared and the effect of the processing operation upon the various components determined. Adjustments may be made to the processing operation based on the comparison.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical,", "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system for measuring an overall dielectric constant of a low-k dielectric film formed over a reflective layer formed over a semiconductor substrate, said system comprising:
   an ellipsometer that measures an electronic component of said overall dielectric constant of said low-k dielectric film and produces a measured electronic component;
   an infrared spectrometer that measures an ionic component of said overall dielectric constant of said low-k dielectric film and produces a measured ionic component;
   a microwave spectrometer that measures said overall dielectric constant of said low-k dielectric film and produces a measured overall dielectric constant by measuring impedance and converting said impedance to said overall dielectric constant; and means for deriving a dipole component of said overall dielectric constant using said measured electronic component, said measured ionic component and said measured overall dielectric constant, wherein a first spectrometer tool includes said infrared spectrometer and said microwave spectrometer, and said ellipsometer and said first spectrometer tool are each non-contact measuring tools.

2. A method for determining an overall dielectric constant of a film comprising:

providing a low-k dielectric film over a reflective layer formed over a substrate;

determining said overall dielectric constant of said low-k dielectric film by measuring said overall dielectric constant without contacting said low-k dielectric film, said measuring including separately measuring an electronic component of said overall dielectric constant, an ionic component of said overall dielectric constant and said overall dielectric constant; and deriving a dipolar component of said overall dielectric constant from said electronic component, said ionic component, and said overall dielectric constant, wherein said measuring said overall dielectric constant includes measuring impedance and converting said impedance to said overall dielectric constant.

3. The method as in claim 2, wherein said low-k dielectric film and said reflective layer are features of an integrated circuit device being formed and further comprising:

further processing said substrate after said determining and said deriving; and completing said integrated circuit device on said substrate.

4. The method as in claim 2, wherein said measuring does not alter any properties of said low-k dielectric film.

5. The method as in claim 2, wherein said reflective layer comprises aluminum or copper.

6. The method as in claim 2, wherein said measuring an electronic component comprises measuring with an ellipsometer; said measuring an ionic component comprises measuring with an infrared spectrometer; and said measuring an overall dielectric constant comprises measuring with a microwave spectrometer.

7. The method as in claim 2, wherein said separately measuring an electronic component is done using radiation having wavelengths in a visible-ultraviolet light range.

8. The method as in claim 2, wherein said separately measuring an ionic component is done using infrared light.

9. The method as in claim 2, wherein said separately measuring an overall dielectric constant is done using microwaves.

10. The method as in claim 2, wherein at least one of measuring an electronic component, measuring an ionic component and measuring an overall dielectric constant includes measuring over a range of wavelengths.

11. The method as in claim 2, wherein said measuring an electronic component includes measuring refractive index and converting said refractive index to said electronic component.

12. The method as in claim 3, wherein said further processing comprises:

processing said substrate in a processing operation then further determining and further deriving following said processing operation;

comparing results of said determining and deriving to said further determining and said further deriving; and adjusting said processing operation based on said comparing.

13. A method for determining an overall dielectric constant of a low-k dielectric film comprising:

providing a low-k dielectric film over a reflective layer formed over a substrate;

determining said overall dielectric constant, an electronic component of said overall dielectric constant, an ionic component of said overall dielectric constant and a dipolar component of said overall dielectric constant without contacting said low-k dielectric film by:

first measuring using an ellipsometer, secondly measuring using an infrared spectrometer and thirdly measuring using a microwave spectrometer and mathematically manipulating results of said first measuring, said secondly measuring and said thirdly measuring, wherein said thirdly measuring comprises measuring said overall dielectric constant by measuring impedance and converting said impedance to said overall dielectric constant.

14. The method as in claim 13, wherein said low-k dielectric film and said reflective layer are features of an integrated circuit device being formed; and further comprising further processing said substrate and completing said integrated circuit device thereon, after said determining.

15. The method as in claim 13, wherein said first measuring comprises measuring said electronic component of said dielectric constant.

16. The method as in claim 13, wherein said first measuring comprises measuring said electronic component of said dielectric constant, said secondly measuring comprises measuring said ionic component of said dielectric constant said thirdly measuring comprises measuring said overall dielectric constant and wherein said dipolar component of said dielectric constant is calculated.

17. The method as in claim 14, wherein said further processing comprises;

processing said substrate in a processing operation and then further determining following said processing operation;

comparing results of said determining to said further determining; and adjusting said processing operation based on said comparing.

* * * * *